(12) United States Patent
Witte et al.

(10) Patent No.: US 6,613,565 B1
(45) Date of Patent: Sep. 2, 2003

(54) USE OF DELTA-LIKE PROTEIN TO INHIBIT THE DIFFERENTIATION OF STEM CELLS

(75) Inventors: Larry Witte, Stormville, NY (US); Bronislaw Pytowski, New York, NY (US); Kateri A. Moore, Princeton, NJ (US); Ihor R. Lemischka, Princeton, NJ (US)

(73) Assignees: ImClone Systems Incorporated, New York, NY (US); Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/142,027

(22) PCT Filed: Mar. 3, 1997

(86) PCT No.: PCT/US97/03520

§ 371 (c)(1),
(2), (4) Date: Dec. 8, 1998

(87) PCT Pub. No.: WO97/31647

PCT Pub. Date: Sep. 4, 1997

Related U.S. Application Data

(63) Continuation-in-part of application No. 08/612,719, filed on Mar. 8, 1996, now abandoned, which is a continuation-in-part of application No. 08/609,533, filed on Mar. 1, 1996, now abandoned.

(51) Int. Cl.$^7$ .............................................. A61K 38/18

(52) U.S. Cl. ....................... 435/372; 435/326; 435/366; 514/2; 514/12; 530/350; 530/351; 530/300

(58) Field of Search ........................ 514/2, 12; 530/350, 530/351, 300; 435/325, 366, 372

(56) References Cited

U.S. PATENT DOCUMENTS

| | | | |
|---|---|---|---|
| 5,580,738 A | * | 12/1996 | Laborda |
| 5,644,031 A | * | 7/1997 | Laborda |

FOREIGN PATENT DOCUMENTS

| | | |
|---|---|---|
| WO | WO 94/13701 | 6/1994 |

OTHER PUBLICATIONS

Bauer et al., Modulated expression of the epidermal growth factor–like homeotic protein dlk influences stromal–cell–pre–B–cell interactions, stromal cell adipogenesis, and pre-–B–cell interleukin–7 requirements, Mole. Cell. Biol., 18(9): 5247–5255, Sep. 1998.*
Moore et al., Hematopoietic acitivity of a stromal cell transmembrane protein containing epidermal growth factor–like repeat motifs, Proc. Natl. Acad. Sci. USA, 94: 4011–4016, Apr. 1997.*
Chitnis et al., "Primary Neurogenesis in Xenopus Embryos Regulated by a Homologue of the Drosophila Neurogenic Gene Delta", Nature, 375, 761–766 (1995).
Dexter et al., "The Structure of the Hemopoietic System," Annu. Rev. Cell Biol., 3, 423–441 (1987).
Henrique et al., "Expression of a Delta Homologue in Prospective Neurons in the Chick", Nature, 375, 787–790 (1995).
Laborda et al., "dlk, a Putative Mammalian Homeotic Gene Differentially Expressed in Small Cell Lung Carcinoma and Neuroendocrine Tumor Cell Line", The Journal of Biological Chemistry, 268, 3817–3820 (1993).
Ellisen et al., "TAN–1, The Human Homolog of the Drosophila Notch Gene, Is Broken by Chromosomal Translocations in T Lymphoblastic Neoplasms," Cell, 66, 649–661 (1991).
Fortini et al., "Notch: Neurogenesis Is Only Part of the Picture", Cell, 75, 1245–1247 (1993).
Lee et al., "dlk, pG2 and Pref–1 mRNAs Encode Similar Proteins Belonging to the EGF–Like Superfamily. Identification of Polymorphic Variants of This RNA", Biochimica et Biophysica Acta, 1261, 223–232 (1995).
Milner et al., "A Human Homologue of the Drosophila Developmental Gene, Notch, Is Expressed in CD34$^+$ Hematopoietic Precursors", Blood, 83, 2057–2062 (1994).
Smas et al., "Pref–1, A Protein Containing EGF–Like Repeats, Inhibits Adipocyte Differentiation", Cell, 73, 725–734 (1993).
Takemoto, "Mouse mRNA For Stromal Cell Derived Protein–1, and Translated Products", GenBank, Submitted (Jul. 22, 1993). Accession No. D16847, published Jan. 15, 1994.
Wharton et al., "Nucleotide Sequence From the Neurogenic Locus Notch Implies a Gene Product That Shares Homology With Proteins Containing EGF–Like Repeats", Cell, 43, 567–581 (1985).
Zipori et al., "Adherent Cells From Mouse Bone Marrow Inhibit the Formation of Colony Simulating Factor (CSF) Induced Myeloid Colonies", Exp. Hematol. 8, 816–817 (1980).
Zipori et al., "Myelopoiesis in the Presence of Stromal Cells From Mouse Bone Marrow: I. Monosaccharides Regulate Colony Formation", Exp. Hematol. 9, 656–663 (1981).

* cited by examiner

*Primary Examiner*—Lorraine Spector
*Assistant Examiner*—Claire M. Kaufman
(74) *Attorney, Agent, or Firm*—Thomas C. Gallagher; Hoffman & Baron LLP

(57) ABSTRACT

Primitive hematopoietic stem cells are closely associated with discrete in vivo microenvironments. These "niches" are thought to provide the molecular signals that mediate stem cell differentiation and self renewal. We have dissected the fetal liver microenvironment into distinct cellular components by establishing an extensive panel of stromal cell lines. One particular cell line maintains repopulating stem cells for prolonged in vitro culture periods. A subtraction cloning strategy has yielded a cDNA which encodes a cell surface glycoprotein with a restricted pattern of expression among stromal cell lines. This molecule, previously identified as dlk/Pref-1, contains EGF-like repeats which are related to those in the Notch/Delta/Serrate family of proteins. We have investigated the potential role of this molecule in hematopoietic stem/progenitor cell regulation. We show that the dlk protein displays activity on purified stem cells by promoting the formation of "cobblestone areas" of proliferation. These cobblestone areas contain both primitive high-proliferative potential progenitors as well as in vivo repopulating stem cells.

16 Claims, 3 Drawing Sheets

```
              3         9        15        21        27        33        39        45
              |         |         |         |         |         |         |         |
   1  GGT GCA ACC CTA GCT TTC TTC CCG CTG GAC GCC CGT GCC CCC TTC
  46  GTG GTC CGC AAC CAG AAG CCC AGC GCA CGC CCC GGA GCA GCC CCT
  91  GCA CCG CCT CCG CTC CCC GGA CCG CGA CCC AGG CCG CCC CGA GAT
 136  GAT CGC GAC CGG AGC CCT CCT GCG CGT CCT CTT GCT CCT GCT GGC
 181  TTT CGG CCA CAG CAC CTA TGG GGC TGA ATG CGA CCC ACC CTG TGA
 226  CCC CCA GTA TGG ATT CTG CGA GGC TGA CAA TGT CTG CAG GTG CCA
 271  TGT TGG CTG GGA GGG TCC CCT CTG TGA CAA GTG TGT AAC TGC CCC
 316  TGG CTG TGT CAA TGG AGT CTG CAA GGA ACC ATG GCA GTG CAT CTG
 361  CAA GGA TGG CTG GGA CGG GAA ATT CTG CGA AAT AGA CGT TCG GGC
 406  TTG CAC CTC AAC CCC CTG CGC CAA CAA TGG AAC TTG CGT GGA CCT
 451  GGA GAA AGG CCA GTA CGA ATG CTC CTG CAC ACC TGG GTT CTC TGG
 496  AAA GGA CTG CCA GCA CAA GGC TGG GCC CTG CGT GAT CAA TGG TTC
 541  TCC CTG CCA GCA CGG AGG CGC CTG CGT GGA TGA TGA GGG CCA GGC
 586  CTC GCA TGC TTC CTG CCT GTG CCC CCC TGG CTT CTC AGG CAA CTT
 631  CTG TGA GAT CGT AGC CGC AAC CAA CAG CTG TAC CCC TAA CCC ATG
 676  CGA GAA CGA TGG CGT CTG CAC CGA CAT CGG GGG TGA CTT CCG TTG
 721  CCG CTG CCC AGC TGG ATT CGT CGA CAA GAC CTG CAG CCG CCC GGT
 766  GAG CAA CTG CGC CAG TGG CCC GTG CCA GAA CGG GGG CAC CTG CCT
 811  CCA GCA CAC CCA GGT GAG CTT CGA GTG TCT GTG CAA GCC CCC GTT
 856  CAT GGG TCC CAC GTG CGC GAA GAA GCG CGG GGC TAG CCC CGT GCA
 901  GGT CAC CCA CCT GCC CAG CGG CTA TGG GCT CAC CTA CCG CCT GAC
 946  CCC CGG GGT GCA CGA GCT GCC TGT TCA GCA GCC CGA GCA ACA CAT
 991  CCT GAA GGT GTC CAT GAA AGA GCT CAA CAA GAG TAC CCC TCT CCT
1036  CAC CGA GGG ACA GGC CAT CTG CTT CAC CAT CCT GGG CGT GCT CAC
1081  CAG CCT GGT GGT GCT GGG CAC CGT GGC CAT CGT CTT TCT CAA CAA
1126  GTG CGA AAC CTG GGT GTC CAA CCT GCG CTA CAA CCA CAC GTT TCG
1171  CAA GAA GAA GAA CCT CCT GTT GCA GTA ACA GCG GCG AGG AGC T
1216  GGC GGT CAA TAT CAT CTT CCC CGA GAA GAT TGA CAT GAC CAC CTT
1261  CAA CAA GGA GGC TGG TGA TGA GGA GAT CTA AGC AGC GTT CCC CAC
1306  CCC CAC TCC CAG GCC CTT CAC CCC GAC CCC GAC CCA GGC CCT CTC
1351  TAT TAC CGG GTT CCT TTA GAG CTC TCT ACC GAG TCT GGC TTT TTG
1396  TGG TGG AGT TTG CTC TAT TGT GTG GAA TCG AGT GAA GCC TAT GCT
1441  TAC ATA TAT TGT CTT GTG TTG CTG TGT GCC ATG CTA CCT CGC TAT
1486  CTA AGA ACC CCT TCC TCC CTA TTA ATG CAT GAT AAT GAA TAA TAA
1531  TAA TAA GAA TTT CAT CTC TAA ATG AAA AAA AAA AAA AAA AAA G
```

FIG. 3

```
              3           9          15          21          27          33          39          45
              |           |           |           |           |           |           |           |
   1  TCT  AAA  GGA  GGT  GGA  GAG  CGC  ACC  GCA  GCC  CGG  TGC  AGC  CCG  GTG
  46  CAG  CCC  TGG  CTT  TCC  CCT  CGC  TGC  GGC  CCG  TGC  CCC  CTT  TCG  CGT
  91  CCG  CAA  CCA  GAA  GCC  CAG  TGC  GGC  GCC  AGG  AGC  CGG  ACC  CGC  GCC
 136  CGC  ACC  GCT  CCC  GGG  ACC  GCG  ACC  CCG  GCC  GCC  CAG  AGA  TGA  CCG
 181  CGA  CCG  AAG  CCC  TCC  TGC  GCG  TCC  TCT  TGC  TCC  TGC  TGG  CTT  TCG
 226  GCC  ACA  GCA  CCT  ATG  GGG  CTG  AAT  GCT  TCC  CGG  CCT  GCA  ACC  CCC
 271  AAA  ATG  GAT  TCT  GCG  AGG  ATG  ACA  ATG  TTT  GCA  GGT  GCC  AGC  CTG
 316  GCT  GGC  AGG  GTC  CCC  TTT  GTG  ACC  AGT  GCG  TGA  CCT  CTC  CCG  GCT
 361  GCC  TTC  ACG  GAC  TCT  GTG  GAG  AAC  CCG  GGC  AGT  GCA  TTT  GCA  CCG
 406  ACG  GCT  GGG  ACG  GGG  AGC  TCT  GTG  ATA  GAG  ATG  TTC  GGG  CCT  GCT
 451  CCT  CGG  CCC  CCT  GTG  CCA  ACA  ACG  GGA  CCT  GCG  TGA  GCC  TGG  ACG
 496  ATG  GCC  TCT  ATG  AAT  GCT  CCT  GTG  CCC  CCG  GGT  ACT  CGG  GAA  AGG
 541  ACT  GCC  AGA  AAA  AGG  ACG  GGC  CCT  GTG  TGA  TCA  ACG  GCT  CCC  CCT
 586  GCC  AGC  ACG  GAG  GCA  CCT  GCG  TGG  ATG  ATG  AGG  GCC  GGG  CCT  CCC
 631  ATG  CCT  CCT  GCC  TGT  GCC  CCC  CTG  GCT  TCT  CAG  GCA  ATT  TCT  GCG
 676  AGA  TCG  TGG  CCA  ACA  GCT  GCA  CCC  CCA  ACC  CAT  GCG  AGA  ACG  ACG
 721  GCG  TCT  GCA  CTG  ACA  TTG  GGG  GCG  ACT  TCC  GCT  GCC  GGT  GCC  CAG
 766  CCG  GCT  TCA  TCG  ACA  AGA  CCT  GCA  GCC  GCC  CGG  TGA  CCA  ACT  GCG
 811  CCA  GCA  GCC  CGT  GCC  AGA  ACG  GGG  GCA  CCT  GCC  TGC  AGC  ACA  CCC
 856  AGG  TGA  GCT  ACG  AGT  GTC  TGT  GCA  AGC  CCG  AGT  TCA  CAG  GTC  TCA
 901  CCT  GTG  TCA  AGA  AGC  GCG  CGC  TGA  GCC  CCC  AGC  AGG  TCA  CCC  GTC
 946  TGC  CCA  GCG  GCT  ATG  GGC  TGG  CCT  ACC  GCC  TGA  CCC  CTG  GGG  TGC
 991  ACG  AGC  TGC  GGG  TGC  AGC  AGC  CGG  AGC  ACC  GCA  TCC  TGA  AGG  TGT
1036  CCA  TGA  AAG  AGC  TCA  ACA  AGA  AAA  CCC  CTC  TCC  TCA  CCG  AGG  GCC
1081  AGG  CCA  TCT  GCT  TCA  CCA  TCC  TGG  GCG  TGC  TCA  CCA  GCC  TGG  TGG
1126  TGC  TGG  GCA  CTG  TGG  GTA  TCG  TCT  TCA  ACA  AGT  GCG  AGA  CCT
1171  GGG  TGT  CCA  ACC  TGC  GCT  ACA  ACC  ACA  TGC  TGC  GGA  AGA  AGA  AGA
1216  ACC  TGC  TGC  TTC  AGT  ACA  ACA  GCG  GGG  AGG  ACC  TGG  CCG  TCA  ACA
1261  TCA  TCT  TCC  CCG  AGA  AGA  TCG  ACA  TGA  CCA  CCT  TCA  GCA  GGG  AGG
1306  CCG  GCG  ACG  AGG  AGA  TCT  AAG  CAG  CGT  TCC  CAC  AGC  CCC  CTC  TAG
1351  ATT  CTT  GGA  GTT  CCG  CAG  AGC  TTA  CTA  TAC  GCG  GTC  TGT  CCT  AAT
1396  CTT  TGT  GGT  GTT  CGC  TAT  CTC  TTG  TGT  CAA  ATC  TGG  TGA  ACG  CTA
1441  CGC  TTA  CAT  ATA  TTG  TCT  TTG  TGC  TGC  TGT  GTG  ACA  AAC  GCA  ATG
1486  CAA  AAA  CAA  TCC  TCT  TTC  TCT  CTC  TTA  ATG  CAT  GAT  ACA  GAA  TAA
1531  TAA  TAA  GAA  TTT  CAT  CTT  TAA  ATG  AG
```

USE OF DELTA-LIKE PROTEIN TO INHIBIT THE DIFFERENTIATION OF STEM CELLS

This application is a CIP of Ser. No. 08/612,719 filed Mar. 8, 1996 abandoned, which is a CIP of Ser. No. 08/609,533, filed Mar. 1, 1996 abandoned.

FIELD OF THE INVENTION

The present invention is directed to the use of Delta-like protein (dlk) to inhibit the rate of differentiation of stem cells.

BACKGROUND OF THE INVENTION

The differentiated cells of some biological systems mature in stages from a common progenitor cell, usually called a stem cell. Such cells include, for example, hematopoietic, neural, epithelial, endothelial, and mesodermal cells.

Stem cells are able to differentiate into mature cells within one of these systems. Differentiation may occur through uncommitted or committed progenitor cell intermediates.

The differentiation of a stem cell may result in one mature cell. Alternatively, a stem cell may differentiate into multiple mature lineages within a biological system, in which case the stem cell is said to be pluripotent. In some cases, the differentiation of a stem cell may result in all the mature lineages of an entire biological system, in which case the stem cell is said to be totipotent. Stem cells are also able to self-renew. The self-renewal must be delicately balanced by differentiation in order to maintain a healthy level of stem cells.

For example, hematopoietic stem cells constitute approximately 0.01% of the cells in adult bone marrow. These stem cells, which can be recognized by the presence of the CD34 antigen, are found in micro-environments associated with stromal cells.

Hematopoietic stem cells are induced by various cytokines, such as c-kit and flk-2/flt-3 ligand, to differentiate into increasingly lineage-committed progenitors. These progenitors differentiate further into the various mature white blood cells, red blood cells, and platelets of the hematopoietic system.

Self-renewal of the stem cells requires their maintenance in an undifferentiated state. There are various applications for methods that increase the time during which stem cell populations remain undifferentiated in vivo and ex vivo. Such applications include, for example, gene therapy, and concentrating stem cell populations.

Another application for maintaining stem cells in an undifferentiated state is cell and tissue transplantation between animals. An example of this application, in the case of hematopoietic cells, is bone marrow transplantation.

Attempts to maintain and expand stem cells, especially hematopoietic stem cells, using various cytokines and cytokine mixtures have been unsuccessful. An object of the present invention is to provide methods for the maintenance of stem cells in an undifferentiated state. A more specific object is to provide methods for the maintenance of hematopoietic stem cells in an undifferentiated state. Another object is to provide a method for enriching a population of stem cells in a mixture of stem cells and non-stem cells.

SUMMARY OF THE INVENTION

These, and other, objects as will be apparent to those having ordinary skill in the art have been met by providing a method for inhibiting the differentiation of stem cells, such as hematopoietic stem cells; and a method for enriching a population of stem cells in a mixture of stem cells and non-stem cells. The methods comprise contacting the stem cells, or the mixture of stem cells and non-stem cells, with a sufficient amount of human delta-like protein (dlk).

BRIEF DESCRIPTION OF THE DRAWINGS

Preferred embodiments of the invention have been chosen for purposes of illustration and description, but are not intended in any way to restrict the scope of the invention. Preferred embodiments of certain aspects of the invention are shown in the accompanying drawings, wherein:

FIG. 1 shows the mouse dlk amino acid sequence (SEQ ID NO: 10) and the human dlk amino acid sequence (SEQ ID NO: 12);

FIG. 2 shows the mouse dlk nucleotide sequence (SEQ ID NO: 11); and

FIG. 3 shows the human dlk nucleotide sequence (SEQ ID NO: 13).

DETAILED DESCRIPTION OF THE INVENTION

The present invention relates to a method for inhibiting the differentiation of stem cells. For the purpose of this application, inhibiting the differentiation of stem cells means preventing, or inhibiting the rate of, the differentiation of stem cells.

A stem cell refers to any cell that is capable of self renewal, and of differentiating into committed progenitors of one or more lineages within a group of cells of a biological system. Such cells include, for example, hematopoietic, neural, epithelial, endothelial, and mesodermal cells. Preferably, the stem cells are capable of re-populating at least one lineage, preferably multiple lineages, and more preferably all lineages of a biological system of cells in an ablated mammal. The method involves contacting the hematopoietic stem cells in vivo or ex vivo with a sufficient amount of delta-like protein (dlk).

The dlk protein and gene is described by Laborda et al. in the Journal of Biological Chemistry 268, 3817–3820 (1993); Lee et al. in Biochimica et Biophysica Acta 1261, 223–232 (1995); and Laborda, International PCT Application WO 94/13701. The dlk gene and protein can be isolated and purified as described in the Laborda et al. and Lee et al. articles and in the Laborda patent application.

Figure 1:
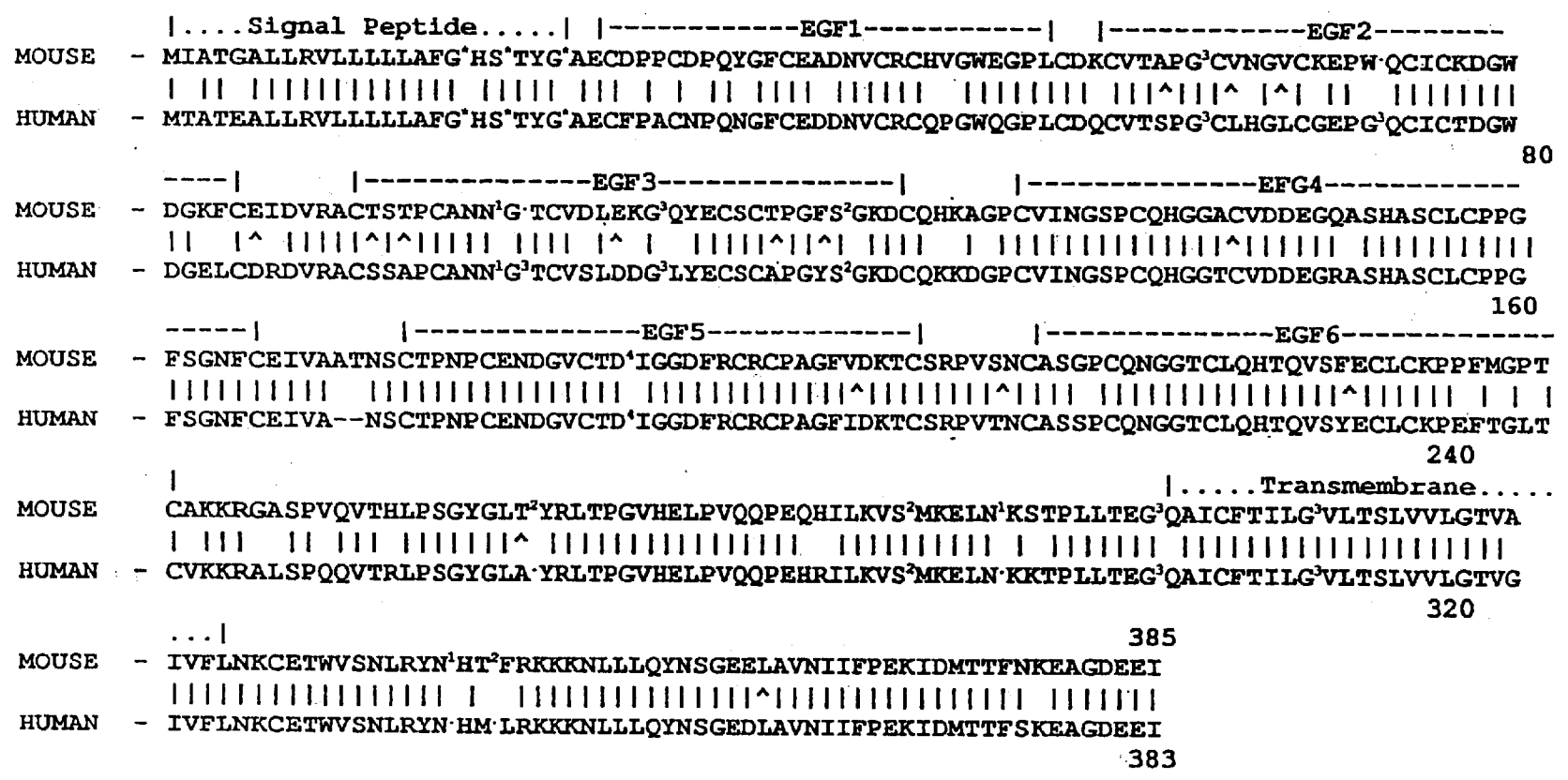

The dlk gene and protein may originate from any mammalian source. The human gene and protein are preferred. The mouse and human dlk amino acid sequences are shown in FIG. 1. The mouse and human dlk nucleotide sequences are shown in FIGS. 2 and 3, respectively.

In addition, the mouse and human dlk amino acid sequences are given in FIGS. 1A and 1B, respectively, of the Laborda patent application; the sequence of mouse and human dlk nucleotide sequence is given in FIGS. 3 and 2, respectively, of the Laborda patent application; and the amino acid and nucleotide sequences of human dlk are given in FIG. 6 of the Lee et al. article.

The dlk gene and protein useful in the present invention may contain mutations and polymorphisms in the sequences as described above. Preferably, the dlk gene and protein are at least about 75% identical, preferably at least about 85%, more preferably at least about 95%, and most preferably at least about 99% identical to the native nucleotide or amino acid sequence of a mammal, such as of the mouse and human sequences described above.

As shown in FIG. 2 of the Laborda et al. article, dlk is a transmembrane protein that contains six EGF-like repeats in an N-terminal extracellular domain and a short C-terminal intracellular domain separated by the transmembrane domain.

The dlk protein useful in the present invention may be a full length protein. Alternatively, the dlk may be in a soluble form (sdlk). The soluble protein may comprise the entire extracellular domain, or at least enough of the extracellular domain for the molecule to retain its biological activity. The extracellular domain should comprise at least three EGF repeats (for example, EGF repeats 1–3, 2–5, or 3–6); preferably at least four EGF repeats (for example, EGF repeats 1–4, 2–5, or 3–6); more preferably five EGF repeats (for example, EGF repeats 1–5, or 2–6); and most preferably all six EGF repeats. The EGF repeats are shown in FIG. 2 of the Laborda et al. article.

The soluble dlk protein preferably lacks both the transmembrane domain and the intracellular domain. Alternatively, the soluble dlk protein may contain all or part of the transmembrane domain and either no part of the intracellular domain, or as much of the intracellular domain that still permits the dlk protein to retain its solubility in water at room temperature.

Soluble forms of dlk can be produced by methods known in the art. For example, the soluble dlk protein may be produced by cloning an appropriate DNA sequence in a suitable expression vector. The DNA is transfected into a suitable host cell, such as, for example, COS, CHO, NIH 3T3, and expressed.

Optionally, the soluble dlk protein is expressed as a fusion protein. Examples of fusion protein partners to be expressed in tandem with the dlk protein include, but are not limited to, IgG protein, metallotheonine, histidine repeats, alkaline phosphatase and FLAG protein.

The dlk protein is then expressed, and preferably secreted directly into the cell media. The protein is harvested, preferably in serum-free media, from the stable expressing cell lines.

The soluble protein can be purified by methods known in the art. A suitable purification method is affinity chromotography.

The purified protein is used for any of the utilities described in the specification The protein can also be used to immunize animals for the production of anti-dlk monoclonal or polyclonal antibodies. Such antibodies can be used to identify and isolate dlk-containing cells, such as stromal cells, that express the dlk protein.

The sdlk may be used in solution. Alternatively, the sdlk may be aggregated by physical means, such as, for example, heat, pH, etc., or chemical means, such as chemical cross linking, as is well known in the art. Such "multivalent" forms of sdlk are better able to cross link the appropriate target molecules on the surface of stem cells, and to provide the appropriate biological signals. The sdlk molecules may also be coated on small, inert beads, such as latex beads for example, or on the surface of a container, such as a culture dish.

If the dlk protein used in the method of the invention contains the transmembrane region, the dlk protein may be attached to the surface of a cell, or may be independent of cells. Some cells, such as some stromal cells, contain surface dlk naturally. An example of such a cell is the stromal cell line known as AFT024.

Alternatively, the cells may not contain surface dlk naturally, but may be transfected with the dlk gene so as to express one or more surface dlk proteins. Some examples of cells suitable to be transfected with the dlk gene include COS, CHO, NIH 3T3, and BFC012.

The dlk protein and its variants, as described above, prevents, or at least inhibits the rate of, the differentiation of hematopoietic stem cells. For this purpose, the dlk protein may be attached to the surface of a stromal cell. Alternatively, the dlk protein may be attached to the surface of a non-stromal cell or may be independent of a cell, in which case it is preferably used in conjunction with stromal cells or other factors, such as those that exist on stromal cells, that, in conjunction with dlk, prevent, or at least inhibit the rate of, the differentiation of hematopoietic stem cells.

The dlk protein and its variants, as described above, may also be used along with a cocktail of growth factors. The cocktail, including the hematopoietic cocktail described below, may be replaced by, or used in conjunction with, 5-fluorouracil.

The growth factors are selected for inclusion in the cocktail so as to be specific for the type of stem cells that are being maintained in an undifferentiated state. The cocktail has the effect of enhancing the inhibition of differentiation, and of inducing the proliferation of the stem cells, leading to self-renewal.

For example, a cocktail of growth factors for hematopoietic stem cells comprises a mixture of one or more of IL-1, G-CSF, GM-CSF, c-kit ligand, IL-3, IL-6, and flk-2/flt-3 ligand. Such cocktails have been described by Moore, et al. in "Ex Vivo Expansion of $CD34^+$ Hematopoietic Progenitors, in Gross, eds.; Advances in Bone Marrow Purging and Processing, Proceeding of the Fourth International Symposium on Bone Marrow Purging and Processing. Orlando, Fla., Wiley-Liss (1994).

The components of the cocktail, the 5-fluorouracil, and the dlk may be used at any concentration at which they are effective. The components of the cocktail and the 5-fluorouracil may, for example, be suitably used at concentrations of 0.1–100 ng/ml, preferably 1–50 ng/ml, and more preferably 5–20 ng/ml. The dlk may, for example, be suitably used at concentrations of 1 ng–100 ug/ml, preferably 0.1–100 ug/ml, more preferably 1–50 ug/ml, and most preferably 5–20 ug/ml.

The dlk protein and its variants as described above may be used on its own, or in conjunction with a cocktail of growth factors, such as a cocktail of hematopoietic growth factors, and/or 5-fluorouracil to prevent, or at least to inhibit the rate of, differentiation ex vivo. The stem cells may be found in a mixture of stem cells and non-stem cells. For example, a mixture of hematopoietic stem cells and more mature, non-stem cells occurs in peripheral blood, bone marrow or umbilical cord blood.

During the increased time the stem cells in the mixture are maintained by the dlk in an undifferentiated state, other, more mature, non-stem cells continue to differentiate, and ultimately die. In this way, the hematopoietic stem cells become enriched and concentrated in the mixture of stem cells and non-stem cells.

For example, a mixture of hematopoietic stem cells, preferably from the bone marrow, may be removed from a patient undergoing chemotherapy or radiation treatment. Patients who will benefit especially are those being treated for cancers, such as those of the white blood cells, i.e. leukemia.

For example, the patient's bone marrow is removed from the patient. The bone marrow is purged of any malignant cells, and the patient is subjected to chemotherapy or radiation treatment. The chemotherapy or radiation treatment depletes the patient's hematopoietic cells.

The hematopoietic stem cells are maintained ex vivo in an undifferentiated state with dlk, as described above. The stem cell population may be expanded at this stage.

Alternatively, the stems cells may be isolated using either negative or positive selection. An example of positive selection is the separation of a stem cell fraction from a larger cell fraction by binding the stems cells to a monoclonal or polyclonal antibody specific to a stem cell antigen, such as CD34. Such antibodies may be bound to microbeads or to a column matrix in order to facilitate the isolation of the stem cells.

An example of negative selection includes passing a cell fraction through a column in which a variety of antibodies directed against mature cell antigens are used to bind the more mature cells, allowing the stem cells lacking these antigens to be separated into a specific fraction. The antibodies may be monoclonal or polyclonal.

Following treatment, the stem cells are reinfused into the patient for self-renewal of the patient's hematopoietic system. The stem cells are preferably derived from the patient undergoing chemotherapy or radiation treatment. If necessary, the stem cells may be derived from a patient other than the patient undergoing chemotherapy or radiation treatment. The patient is a mammal, preferably a human.

Alternatively, the stem cells may be removed from a patient and subjected to gene therapy while the cells are maintained in an undifferentiated state by the dlk protein, or a variant, as described above. The presence of the dlk increases the length of time a stem cell is available for gene therapy.

In vivo, the dlk, preferably sdlk, may be used to expand the available pool of hematopoietic stem cells. Such treatment is of benefit before chemotherapy or radiotherapy for various malignancies. Increased stem cell populations would allow a more rapid re-population of all blood cells, including leukocytes and platelets, that are typically depleted during such therapies.

dlk may be administered to patients by methods known in the art. Preferably, sdlk is administered by intravenous injection, or is injected directly into the bone marrow cavity.

EXAMPLES

Example 1

Soluble dlk

1. A full-length cDNA clone for human dlk (hdlk) was obtained as described above. A soluble dlk (sdlk) expression construct was prepared by PCR by truncating the cDNA before the first codon of the predicted transmembrane domain. The positive (5') primer (Primer 1) was located starting eight nucleotides 5' of the ATG codon, and encoded a Hind III restriction site. The negative (3') primer (primer 2) introduced a stop codon and a Not 1 site immediately following the codon for the ultimate alanine in the extracellular domain of human dlk. The sequences of these primers are given below. The resulting PCR fragment was cloned into the eukaruotic expression vector pcDNA3 (Invitrogen Inc.). Protein expression was achieved by introducing the expression plasmid into NIH 3T3 and CHO cells and establishing permanent lines of expressing cells. In parallel, constructs directing the expression of sdlk were joined to sequences expressing the coding regions for alkaline phosphatase and for the Fc region of human 1gG1. The resulting fusion proteins (sdlk-AP and sDlk-1g) were expressed as indicated above for sdlk. These fusion proteins can be easily purified and used in several types of binding and functional assays.

Primer 1: 5'-GAG.GGT.ACC.AAG.CTT.CCA.GAG.ATG.AC-C.GCG.ACC.GA (SEQ ID NO: 1)

Primer 2: 5'GCA.TCT.AGA.GCG.GCC.GCT.CAG.GCC.TGT.C-CC.TCG GTG.AGG.AG (SEQ ID NO: 2)

Example 2

Cell Lines and Culture

The AFT024 and BFC012 stromal cell lines were characterized for their ability to support highly enriched fetal liver and adult bone marrow stem cells using both in vitro and in vivo assays. Cells were routinely cultured in Dulbecco's modified Eagle's medium (DMEM) containing 10% fetal bovine serum (FBS) and 50 mM b-mercaptoethanol (BME), and maintained at 31°–33° C., 5% $CO_2$. For long-term cocultures with hematopoietic stem cells, confluent monolayers were irradiated (20 Gy), placed in modified Dexter media (DMEM, 10% FBS, 10% horse serum, 50 mM BME, 0.1 mM hydrocortisone) and maintained at 37° C., 5% $CO_2$ with weekly media changes. NIH 3T3 cells were obtained from ATCC.

Example 3 dlk Expression Analysis

Total RNAs from stromal cell lines were poly $A^+$ selected, Northern blotted, and hybridized to $^{32}P$-labeled probes according to standard protocols. A 600 bp dlk cDNA clone from the AFT024 subtracted library was used as a probe. cDNA templates for RT-PCR were prepared using Super-Script reverse transcriptase according to manufacturer's protocols (GibcoBRL). Oligonucleotide primers for the dlk PCR reactions were: sense 5'- GACCCAGGCTGCCCC-3' (SEQ ID NO: 3) and antisense 5'-GGTACTCTTGTTGAG-3' (SEQ ID NO: 4). For analysis of dlk expression at the protein level, antisera specific for dlk was generated by immunizing rabbits with a Flag-dlk fusion protein (described below). Resultant antibodies were purified by affinity chromatography on Sepharose C1-4B to which dlk-Ig (described below) was coupled according to the manufacturer's instructions (Pharmacia Biotech Inc.). After elution and neutralization, affinity purified dlk antibodies were dialyzed against phosphate buffered saline (PBS) and protein concentration was determined by the BCA method (Pierce). Cell surface expression of dlk in native and transfected (see below) stromal cell lines was accomplished by flow cytometry with the affinity purified dlk antibody. Stromal cell lines in active growth phase were washed once with PBS/0.5 mM EDTA, and harvested by trituration in PBS/EDTA. Twice washed (PBS/3%FBS) cells were incubated with dlk antibody and a similarily prepared irrelevant control antibody. Specific labeling was developed by donkey anti-rabbit-FITC (Jackson Inmunoresearch). Stained cells were analyzed on a Becton Dickinson FACScan using Cell Quest software.

Example 4 dlk Fusion Protein Preparation

The expression plasmid pCD4-Ig contains cDNA for the extracellular domain of human CD4 fused to genomic sequences of the human immunoglobin heavy chain. This cDNA was cloned into EcoRI and Not I sites of pcDNA3 (Invitrogen) to give the plasmid KB52.3.2. cDNA encoding the extracellular domain of dlk was obtained by RT-PCR with primers BP 151 and BP 152 using total RNA from NIH 3T3 cells as template. The primer BP 152 includes the last codon in the dlk extracellular domain and contains an EcoRI site in frame with that of KB52.3.2. The resulting PCR fragment was cloned into KB52.3.2 via Hind III and EcoRI sites to obtain the soluble dlk-Ig expression plasmid. pdlk-Ig or pCD4-Ig were transfected into NIH 3T3 cells together with pSVNeo and stable clones were isolated after selection in 400 mg/ml G418 (active wt., GibcoBRL) in DMEM, 10% FBS. Primers; sense BP 151: 5'GAGGGTACCAAGCT TCGTGGTCCGCAACCAGAAG-3' (SEQ ID NO: 5); antisense BP 152: 5'CTCAGATCTGAATTCGGCCTGTC-CCTCGG TGAGGAG-3' (SEQ ID NO: 6).

The CD4-Ig and dlk-Ig proteins were harvested in serum-free media from stable expressing cell lines. The soluble fusion proteins were purified by affinity chromatography on HiTrap Protein G-sepharose (Pharmacia Biotech Inc.) equilibrated with 0.1 M Tris-HCl, pH 7.6, 0.5 M NaCl and eluted with 0.2 M glycine-HCl, pH 2.8, 0.5 M NaCl. Eluted protein was dialyzed against PBS. Protein concentration was determined by the BCA method (Pierce).

Flag-dlk fusion protein was used to immunize rabbits for the production of dlk antiserum. The protein expression plasmid pcDNA3-Flag is a modification of the plasmid pcDNA3 (Invitrogen) and contains 22 base pairs of 5' untranslated sequence, a preprotrypsinogen signal sequence, and the coding region for the Flag peptide (DYKDDDDKI) as well as a Bgl II restriction site. A cDNA fragment encoding the extracellular domain of dlk was obtained by RT-PCR using RNA from NIH3T3 cells. The 5' primer (BP155) was designed to introduce an in frame Bgl II site at the 5' end of the predicted mature dlk protein coding sequence. The 3' primer (BP154) contained Xba I and Not I sites downstream of a stop codon which is immediately adjacent to the last amino acid of the predicted dlk extracellular domain. Primers; sense BP 155: 5'-GACAAGATC TCAGCTGAATAGCGACCCACCCTGTG-3' (SEQ ID NO: 7); antisense BP 154: 5'-GCATCTAGAGCGGCCGCT CAGGCCTGTCCCTCGGTGAGGAG-3' (SEQ ID NO: 8). The PCR fragment was digested with Bgl II and Not I and ligated into pcDNA3-Flag to yield pFlag-dlk. pFlag-dlk was transfected into COS cells using DEAE-dextran. Affinity purification of the Flag-dlk protein from COS conditioned media was performed according to manufacturer's directions using the Flag monoclonal antibody, M1, immobilized on agarose (International Biotechnologies).

Example 5

Plasmid Constructs and Stable Transfection

Full-length murine dlk cDNA was obtained by RT-PCR with primers BP 151 (SEQ ID: NO 5, see above) and antisense BP 200:

```
5' GCATCTAGAGCGGCCGCGAACGCTGCTTAGA
    TCTCCT-3'                        (SEQ ID NO: 9),
``` using total RNA from NMH3T3 cells as template. Sequencing confirmed that the resulting product was identical to the published dlk sequence. The product was subcloned into the vector pCRII (Invitrogen) and then cloned into a retroviral expression vector via the primer-encoded HindIII and NotI sites. Supercoiled plasmid was transfected into BFC012 stromal cells by the calcium phosphate method, according to the manufacturer's protocol (GibcoBRL) together with the pZeo (Invitrogen) selectable marker and selected in 50 mg/ml Zeocin (Invitrogen). BFC012 cells were also transfected with pZeo alone and selected as above. Clones from both selected populations were isolated and all remaining colonies (100–200/dish) were pooled and expanded as populations.

Example 6

Hematopoietic Stem Cells and in vitro Hematopoietic Assays

Hematopoietic stem cell populations were derived from wild type, Ly5.2-C57B1/6J (Jackson Laboratories), day 14 fetal liver, enriched for the AA4.1$^+$, Sca-1$^+$, c-kit$^+$, and lin$^{lo/-}$ phenotype, by immunopanning and fluorescence-activated cell sorting. Adult bone marrow (BM) was used directly after density centrifugation and immunomagnetic bead depletion or was further enriched for Sca-1$^+$, c-kit$^+$, lin$^{lo/-}$ cells by flow cytometry as described. Cell sorting and data analysis was accomplished with a Becton Dickinson FACS Vantage using Cell Quest Software. Stromal cell/stem cell cocultures were initiated in 12-well trays with 300–1000 enriched stem cells per well. Cobblestone areas were quantitated by inverted-phase microscopy as described. Clonogenic progenitor assays were performed with either freshly purified stem cells or cells harvested from the stromal cocultures. These were cultured in cytokine-containing semisolid media according to the manufacturer's recommendations (Stem Cell Technologies). Progenitor colonies were scored after 8–12 days according to established criteria. Soluble dlk and control fusion proteins were added to semisolid progenitor assays at concentrations of 0.1, 0.5 and 1.0 mg/ml and also to BFC012 stromal cocultures at concentrations of 0.1 mg/ml. Fusion protein was replenished weekly in the stromal cocultures.

Example 7

Competitive Repopulating Transplantation Assay

Cultured cells were harvested, combined with fresh unfractionated BM obtained from congenic C57B1/6 Ly5.1 mice (National Cancer Institute) and transplanted into lethally irradiated (10 Gy, split dose 3 hours apart from a $^{137}$CS source, 1 Gy/min) Ly5.1 recipient mice. Each mouse received 2×10$^5$ competitor BM cells and a fraction of the cocultured stem cells. Mice were bled by capillary puncture of the orbital venous plexus and 100 ml were collected into heparin-containing (10 U/ml) DMEM; red blood cells were removed by NH$_4$Cl lysis. The nucleated cells were stained for the Ly5.2 (CD45.2) allelic marker using either FITC-labeled directly conjugated Ly5.2 monoclonal antibody or a biotinylated form developed with streptavidin conjugated to Texas Red. Cells were also stained with directly conjugated antibodies to lineage markers. All antibodies and chromogens were obtained from Pharmingen. Flow cytometric analysis was done on a Becton Dickinson FACS Vantage using Cell Quest Software.

Supplemental Enablement

The invention as claimed is enabled in accordance with the specification and readily available references and starting materials.

Nevertheless, on Mar. 3, 1997, Applicants have deposited with the American Type Culture Collection, 10801 University Boulevard, Manassas, Va. 20110-2209 (ATCC) transfected cell line BFC012, under ATCC Accession Number CRL-12308. This deposit was made under the provisions of the Budapest Treaty on the International Recognition of the Deposit of Microorganisms for the Purposes of Patent Procedure and the regulations thereunder (Budapest Treaty). This assures maintenance of a viable culture for thirty years from date of deposit. The organisms will be made available by ATCC under the terms of the Budapest Treaty, and subject to an agreement between Applicants and ATCC, which assures unrestricted availability upon issuance of the pertinent U.S. patent. Availability of the deposited strains is not to be construed as a license to practice the invention in contravention of the rights granted under the authority of any government in accordance with its patent laws.

We claim:

1. A method for inhibiting the differentiation of hematopoietic stem cells, comprising contacting the stem cells in vitro or ex vivo with an amount of dlk protein sufficient to inhibit the differentiation of the stem cells, wherein the dlk protein is at least about 95% identical to the sequence shown as SEQ ID NO:10 or SEQ ID NO: 12.

2. A method according to claim 1 wherein the stem cells are totipotent.

3. A method according to claim 1 wherein the stem cells are pluripotent.

4. A method according to claim 1 wherein the dlk protein is human dlk protein.

5. A method according to claim 1 that takes place ex vivo.

6. A method according to claim 5 wherein the hematopoietic stem cells are in the peripheral blood, bone marrow, or cord blood of a human.

7. A method according to claim 1 wherein the dlk is used in conjunction with a cocktail of growth factors specific for said stem cells.

8. A method according to claim 1 wherein the dlk is used in conjunction with a cocktail of growth factors for hematopoietic stem cells.

9. A method according to claim 1 wherein the dlk is used in conjunction with 5-fluorouracil.

10. A method according to claim 1 wherein the dlk protein is not attached to a cell.

11. A method according to claim 10 wherein the dlk protein is soluble dlk protein.

12. A method according to claim 1 wherein the dlk protein is attached to the surface of a cell.

13. A method according to claim 12 wherein the cell is a stromal cell.

14. A method according to claim 13 wherein the stromal cell is a BFC012 cell transfected with the dlk gene to express one or more surface dlk proteins, the transfected BFC012 cell deposited under Accession Number CRL-12308.

15. A method for enriching a population of stem cells in a mixture of stem cells and non-stem cells comprising contacting the mixture in vitro or ex vivo with an amount of human dlk protein sufficient to inhibit the differentiation of the stem cells, wherein the stem cells are hematopoietic stem cells and the dlk protein is at least about 95% identical to the sequence shown as SEQ ID NO: 12.

16. A method according to claim 15 wherein the dlk is used in conjunction with a cocktail of growth factors for hematopoietic stem cells.

* * * * *

```
                            SEQUENCE LISTING

<160> NUMBER OF SEQ ID NOS:  13

<210> SEQ ID NO 1
  <211> LENGTH: 35
  <212> TYPE: DNA
  <213> ORGANISM: Human

<400> SEQUENCE: 1
gagggtacca agcttccaga gatgaccgcg accga                                  35

<210> SEQ ID NO 2
  <211> LENGTH: 41
  <212> TYPE: DNA
  <213> ORGANISM: Human

<400> SEQUENCE: 2
gcatctagag cggccgctca ggcctgtccc tcggtgagga g                           41

<210> SEQ ID NO 3
  <211> LENGTH: 15
  <212> TYPE: DNA
  <213> ORGANISM: Murine

<400> SEQUENCE: 3
gacccaggct gcccc                                                        15

<210> SEQ ID NO 4
  <211> LENGTH: 15
  <212> TYPE: DNA
  <213> ORGANISM: Murine

<400> SEQUENCE: 4
ggtactcttg ttgag                                                        15

<210> SEQ ID NO 5
  <211> LENGTH: 34
  <212> TYPE: DNA
  <213> ORGANISM: Murine

<400> SEQUENCE: 5
gagggtacca agcttcgtgg tccgcaacca gaag                                   34

<210> SEQ ID NO 6
  <211> LENGTH: 36
  <212> TYPE: DNA
  <213> ORGANISM: Human

<400> SEQUENCE: 6
ctcagatctg aattcggcct gtccctcggt gaggag                                 36

<210> SEQ ID NO 7
  <211> LENGTH: 35
  <212> TYPE: DNA
  <213> ORGANISM: Murine

<400> SEQUENCE: 7
```

```
gacaagatct cagctgaata gcgacccacc ctgtg                                35
```

<210> SEQ ID NO 8
<211> LENGTH: 41
<212> TYPE: DNA
<213> ORGANISM: Human

<400> SEQUENCE: 8

```
gcatctagag cggccgctca ggcctgtccc tcggtgagga g                         41
```

<210> SEQ ID NO 9
<211> LENGTH: 37
<212> TYPE: DNA
<213> ORGANISM: Human

<400> SEQUENCE: 9

```
gcatctagag cggccgcgaa cgctgcttag atctcct                              37
```

<210> SEQ ID NO 10
<211> LENGTH: 385
<212> TYPE: PRT
<213> ORGANISM: Mouse

<400> SEQUENCE: 10

```
Met Ile Ala Thr Gly Ala Leu Leu Arg Val Leu Leu Leu Leu Leu Ala
 1               5                  10                  15

Phe Gly His Ser Thr Tyr Gly Ala Glu Cys Asp Pro Pro Cys Asp Pro
                20                  25                  30

Gln Tyr Gly Phe Cys Glu Ala Asp Asn Val Cys Arg Cys His Val Gly
            35                  40                  45

Trp Glu Gly Pro Leu Cys Asp Lys Cys Val Thr Ala Pro Gly Cys Val
 50                  55                  60

Asn Gly Val Cys Lys Glu Pro Trp Gln Cys Ile Cys Lys Asp Gly Trp
 65                  70                  75                  80

Asp Gly Lys Phe Cys Glu Ile Asp Val Arg Ala Cys Thr Ser Thr Pro
                85                  90                  95

Cys Ala Asn Asn Gly Thr Cys Val Asp Leu Glu Lys Gly Gln Tyr Glu
            100                 105                 110

Cys Ser Cys Thr Pro Gly Phe Ser Gly Lys Asp Cys Gln His Lys Ala
        115                 120                 125

Gly Pro Cys Val Ile Asn Gly Ser Pro Cys Gln His Gly Gly Ala Cys
    130                 135                 140

Val Asp Asp Glu Gly Gln Ala Ser His Ala Ser Cys Leu Cys Pro Pro
145                 150                 155                 160

Gly Phe Ser Gly Asn Phe Cys Glu Ile Val Ala Ala Thr Asn Ser Cys
                165                 170                 175

Thr Pro Asn Pro Cys Glu Asn Asp Gly Val Cys Thr Asp Ile Gly Gly
            180                 185                 190

Asp Phe Arg Cys Arg Cys Pro Ala Gly Phe Val Asp Lys Thr Cys Ser
        195                 200                 205

Arg Pro Val Ser Asn Cys Ala Ser Gly Pro Cys Gln Asn Gly Gly Thr
    210                 215                 220

Cys Leu Gln His Thr Gln Val Ser Phe Glu Cys Leu Cys Lys Pro Pro
225                 230                 235                 240

Phe Met Gly Pro Thr Cys Ala Lys Lys Arg Gly Ala Ser Pro Val Gln
                245                 250                 255
```

```
Val Thr His Leu Pro Ser Gly Tyr Gly Leu Thr Tyr Arg Leu Thr Pro
            260                 265                 270

Gly Val His Glu Leu Pro Val Gln Gln Pro Glu Gln His Ile Leu Lys
        275                 280                 285

Val Ser Met Lys Glu Leu Asn Lys Ser Thr Pro Leu Leu Thr Glu Gly
        290                 295                 300

Gln Ala Ile Cys Phe Thr Ile Leu Gly Val Leu Thr Ser Leu Val Val
305                 310                 315                 320

Leu Gly Thr Val Ala Ile Val Phe Leu Asn Lys Cys Glu Thr Trp Val
                325                 330                 335

Ser Asn Leu Arg Tyr Asn His Thr Phe Arg Lys Lys Asn Leu Leu
            340                 345                 350

Leu Gln Tyr Asn Ser Gly Glu Leu Ala Val Asn Ile Ile Phe Pro
            355                 360                 365

Glu Lys Ile Asp Met Thr Thr Phe Asn Lys Glu Ala Gly Asp Glu Glu
    370                 375                 380

Ile
385

<210> SEQ ID NO 11
<211> LENGTH: 1158
<212> TYPE: DNA
<213> ORGANISM: Mouse

<400> SEQUENCE: 11
atgatcgcga ccggagccct cctgcgcgtc ctcttgctcc tgctggcttt cggccacagc      60
acctatgggg ctgaatgcga cccaccctgt gaccccagt atggattctg cgaggctgac     120
aatgtctgca ggtgccatgt tggctgggag gtcccctct gtgacaagtg tgtaactgcc      180
cctggctgtg tcaatggagt ctgcaaggaa ccatggcagt gcatctgcaa ggatggctgg     240
gacgggaaat tctgcgaaat agacgttcgg gcttgcacct caaccccctg cgccaacaat     300
ggaacttgcg tggacctgga aaaggccag tacgaatgct cctgcacacc tgggttctct     360
ggaaaggact gccagcacaa ggctgggccc tgcgtgatca atggttctcc ctgccagcac     420
ggaggcgcct cgtggatga tgagggccag gcctcgcatg cttcctgcct gtgcccccct     480
ggcttctcag caacttctg tgagatcgta gccgcaacca cagctgtac ccctaaccca     540
tgcgagaacg atggcgtctg caccgacatc ggggtgact tccgttgccg ctgcccagct     600
ggattcgtcg acaagacctg cagccgcccg gtgagcaact gcgccagtgg cccgtgccag     660
aacgggggca cctgcctcca gcacacccag gtgagcttcg agtgtctgtg caagcccccg     720
ttcatgggtc ccacgtgcgc gaagaagcgc ggggctagcc ccgtgcaggt cacccacctg     780
cccagcggct atgggctcac ctaccgcctg accccgggg tgcacgagct gcctgttcag     840
cagcccgagc aacacatcct gaaggtgtcc atgaaagagc tcaacaagag taccctctc     900
ctcaccgagg gacaggccat ctgcttcacc atcctgggcg tgctcaccag cctggtggtg     960
ctgggcaccg tggccatcgt ctttctcaac aagtgcgaaa cctgggtgtc caacctgcgc    1020
tacaaccaca cgtttcgcaa gaagaagaac ctcctgttgc agtataacag cggcgaggag    1080
ctggcggtca atatcatctt ccccgagaag attgacatga ccaccttcaa caaggaggct    1140
ggtgatgagg agatctaa                                                  1158

<210> SEQ ID NO 12
<211> LENGTH: 383
<212> TYPE: PRT
```

<213> ORGANISM: Human

<400> SEQUENCE: 12

```
Met Thr Ala Thr Glu Ala Leu Leu Arg Val Leu Leu Leu Leu Leu Ala
 1               5                   10                  15

Phe Gly His Ser Thr Tyr Gly Ala Glu Cys Phe Pro Ala Cys Asn Pro
                20                  25                  30

Gln Asn Gly Phe Cys Glu Asp Asp Asn Val Cys Arg Cys His Val Gly
            35                  40                  45

Trp Gln Gly Pro Leu Cys Asp Gln Cys Val Thr Ser Pro Gly Cys Leu
     50                  55                  60

His Gly Leu Cys Gly Glu Pro Gly Gln Cys Ile Cys Thr Asp Gly Trp
 65                  70                  75                  80

Asp Gly Glu Leu Cys Asp Arg Asp Val Arg Ala Cys Ser Ser Ala Pro
                85                  90                  95

Cys Ala Asn Asn Gly Thr Cys Val Ser Leu Asp Gly Leu Tyr Glu
                100                 105                 110

Cys Ser Cys Ala Pro Gly Tyr Ser Gly Lys Asp Cys Gln Lys Asp
            115                 120                 125

Gly Pro Cys Val Ile Asn Gly Ser Pro Cys Gln His Gly Gly Thr Cys
     130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
     195                 200                 205

Val Thr Asn Cys Ala Ser Ser Pro Cys Gln Asn Gly Gly Thr Cys Leu
210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255

Arg Leu Pro Ser Gly Tyr Gly Leu Ala Tyr Arg Leu Thr Pro Gly Val
            260                 265                 270

His Glu Leu Pro Val Gln Gln Pro Glu His Arg Ile Leu Lys Val Ser
     275                 280                 285

Met Lys Glu Leu Asn Lys Lys Thr Pro Leu Leu Thr Glu Gly Gln Ala
290                 295                 300

Ile Cys Phe Thr Ile Leu Gly Val Leu Thr Ser Leu Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Asn Leu Leu Leu Gln
            340                 345                 350

Tyr Asn Ser Gly Glu Asp Leu Ala Val Asn Ile Ile Phe Pro Glu Lys
     355                 360                 365

Ile Asp Met Thr Thr Phe Ser Lys Glu Ala Gly Asp Glu Glu Ile
370                 375                 380
```

<210> SEQ ID NO 13
<211> LENGTH: 1158

-continued

```
<212> TYPE: DNA
<213> ORGANISM: Human

<400> SEQUENCE: 13
atgatcgcga ccggagccct cctgcgcgtc ctcttgctcc tgctggcttt cggccacagc      60
acctatgggg ctgaatgcga cccaccctgt gaccccagt atggattctg cgaggctgac      120
aatgtctgca ggtgccatgt tggctgggag ggtcccctct gtgacaagtg tgtaactgcc     180
cctggctgtg tcaatggagt ctgcaaggaa ccatggcagt gcatctgcaa ggatggctgg     240
gacgggaaat tctgcgaaat agacgttcgg gcttgcacct caaccccctg cgccaacaat     300
ggaacttgcg tggacctgga gaaaggccag tacgaatgct cctgcacacc tgggttctct     360
ggaaaggact gccagcacaa ggctgggccc tgcgtgatca atggttctcc ctgccagcac     420
ggaggcgcct gcgtggatga tgagggccag gcctcgcatg cttcctgcct gtgccccct     480 ggcttctcag gcaacttctg tgagatcgta gccgcaacca acagctgtac ccctaaccca    540
tgcgagaacg atggcgtctg caccgacatc ggggtgact tccgttgccg ctgcccagct     600
ggattcgtcg acaagacctg cagccgcccg gtgagcaact gcgccagtgg cccgtgccag    660
aacgggggca cctgcctcca gcacacccag gtgagcttcg agtgtctgtg caagcccccg    720
ttcatgggtc ccacgtgcgc gaagaagcgc ggggctagcc ccgtgcaggt cacccacctg    780
cccagcggct atgggctcac ctaccgcctg accccggggg tgcacgagct gcctgttcag    840
cagcccgagc aacacatcct gaaggtgtcc atgaaagagc tcaacaagag tacccctctc    900
ctcaccgagg gacaggccat ctgcttcacc atcctgggcg tgctcaccag cctggtggtg    960
ctgggcaccg tggccatcgt ctttctcaac aagtgcgaaa cctgggtgtc caacctgcgc   1020
tacaaccaca cgtttcgcaa gaagaagaac ctcctgttgc agtataacag cggcgaggag   1080
ctggcggtca atatcatctt ccccgagaag attgacatga ccaccttcaa caaggaggct   1140
ggtgatgagg agatctaa                                                  1158
```